(12) United States Patent
Hirofuji et al.

(10) Patent No.: US 8,785,406 B2
(45) Date of Patent: Jul. 22, 2014

(54) STABILIZED AND LYOPHILIZED FORMULATION OF ANTHRACYCLINE COMPOUNDS

(75) Inventors: Hajimu Hirofuji, Niihama (JP); Hotaka Hashimoto, Ibaraki (JP); Kazunari Tanaka, Ibaraki (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 13/322,151

(22) PCT Filed: May 27, 2009

(86) PCT No.: PCT/JP2009/059682
§ 371 (c)(1),
(2), (4) Date: Nov. 22, 2011

(87) PCT Pub. No.: WO2010/137131
PCT Pub. Date: Dec. 2, 2010

(65) Prior Publication Data
US 2012/0077768 A1    Mar. 29, 2012

(51) Int. Cl.
*A61K 31/70* (2006.01)

(52) U.S. Cl.
USPC .............................................. 514/34; 536/6.4

(58) Field of Classification Search
USPC ............................................ 535/6.4; 514/34
See application file for complete search history.

(56) References Cited

U.S. PATENT DOCUMENTS

| 4,673,668 A | 6/1987 | Ishizumi et al. |
| 4,952,566 A | 8/1990 | Sakamaki et al. |
| 6,376,469 B1 | 4/2002 | Shimago et al. |
| 2004/0249137 A1 | 12/2004 | Takahashi et al. |
| 2006/0003949 A1 | 1/2006 | Hirofuji et al. |

FOREIGN PATENT DOCUMENTS

| EP | 302729 B1 | 1/1992 |
| JP | 03005397 A | 1/1991 |
| WO | WO-9928331 A3 | 7/1999 |
| WO | WO-03/035660 A1 | 5/2003 |
| WO | WO-2004/050098 A1 | 6/2004 |

OTHER PUBLICATIONS

Extended European Search Report dated Oct. 1, 2012, issued in corresponding European Application No. 09845198.2.
USP 25/NF 20 (2002), p. 506, p. 617, p. 889, (The Pharmacopeia of the United States, 25th Revision, Daunorubicin Hydrochloride for Injection (p. 506), Doxorubicin Hydrochloride for Injection (p. 617) and Idarubicin Hydrochloride for Injection (p. 889)).
Pharmaceutics, 4th Edition, p. 267, first paragraph, (1999).
16th Edition of Remington's Pharmaceutical Sciences, Mack Publishing Co., p. 1483, (1980).
USPTO Decision on Appeal for U.S. Appl. No. 10/536,397 dated Feb. 22, 2012.

*Primary Examiner* — Elli Peselev
(74) *Attorney, Agent, or Firm* — Birch, Stewart, Kolasch & Birch, LLP

(57) ABSTRACT

The present invention provides a lyophilized amrubicin formulation and a process thereof. In the process, the concentration of the aqueous solution before lyophilization is controlled to about 7.5 mg(potency)/mL or more. Thus, the formulation decreases the production of desaccharified compound and is stable to storage for a long period. The formulation is useful as a cancer chemotherapeutic agent.

9 Claims, 2 Drawing Sheets

STABILIZED AND LYOPHILIZED FORMULATION OF ANTHRACYCLINE COMPOUNDS

This application is the National Stage under 35 U.S.C. §371 of International Application Number PCT/JP2009/059682, which was filed on May 27, 2009.

TECHNICAL FIELD

The present invention relates to a stabilized formulation, especially a lyophilized formulation, comprising amrubicin or a pharmaceutically acceptable salt thereof wherein amrubicin is useful as a cancer chemotherapeutic agent. Furthermore, the present invention relates to a process of the formulation, especially the lyophilized formulation, comprising amrubicin or a pharmaceutically acceptable salt thereof.

BACKGROUND ART

It is known that (7S,9S)-9-acetyl-9-amino-7-[(2-deoxy-β-D-erythro-pentopyranosyl)oxy]-7,8,9,10-tetrahydro-6,11-dihydroxy-5,12-naphthacenedione which has the following Formula (1):

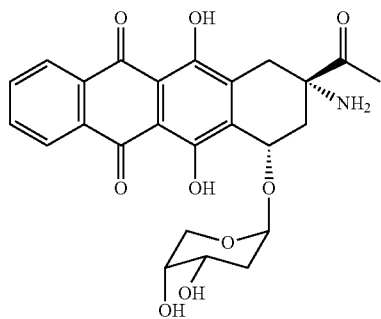

(1)

(hereinafter, referred to as amrubicin) and a salt thereof are useful as a cancer chemotherapeutic agent (see, Patent Reference 1). It is also known that there are several crystal forms of amrubicin hydrochloride, and one of them has a high thermostability (see, Patent Reference 2).

Anthracycline compounds such as amrubicin are unstable in a solution. When formulating such compounds as an injection, generally, they are put into a vial as a powder or lyophilized to prepare an injection formulation wherein the compound is to be dissolved before use.

Furthermore, as a stabilized formulation of amrubicin, the formulation comprising L-cysteine or a salt thereof is known (see, Patent Reference 3 and Patent Reference 4).

[Patent Reference 1] JP 1992(3)-5397 A (Corresponding U.S. Pat. No. 4,673,668 B)

[Patent Reference 2] JP 2975018 B (Corresponding U.S. Pat. No. 6,376,469 B)

[Patent Reference 3] JP 2603480 B (Corresponding U.S. Pat. No. 4,952,566 B)

[Patent Reference 4] WO 2004/050098

(Corresponding US patent application: US 2006/0003949 A)

SUMMARY OF INVENTION

Technical Problem

It is known that representative degradation products of amrubicin are a desaccharified compound of the following Formula (2):

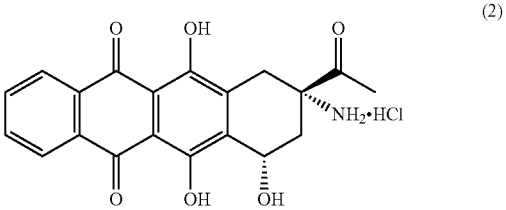

(2)

[hereinafter, referred to as Desaccharified Compound (2)] and a deaminated compound of the following Formula (3):

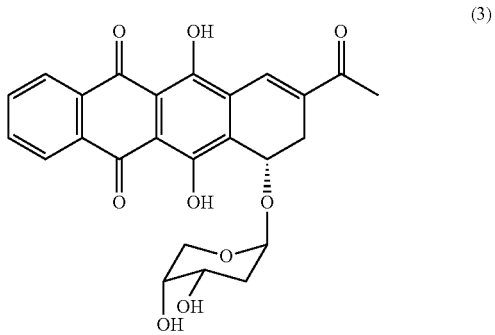 [SMILES: CC(=O)C1=Cc2c(O)c3c(c(O)c2[C@@H](OC2CC(O)C(O)CO2)C1)C(=O)c1ccccc1C3=O]

(3)

[hereinafter, referred to as Deaminated Compound (3)]. The degradation products tend to increase during the processes of preparing and storing the amrubicin formulation. Thus, from the viewpoint of pharmaceutical quality assurance, it is extremely important to suppress the increase of the degradation products for a long period as much as possible, and there had been a desire to develop a method to further stabilize the amrubicin formulation.

On the other hand, as previously mentioned, a method of adding L-cysteine or a salt thereof to the formulation is known as a technique to stabilize the amrubicin formulation (Patent Reference 3). Although the production of Deaminated Compound (3) can be suppressed by the method, in some cases the production of Desaccharified Compound (2) increased depending on conditions. Accordingly, the purpose of the present invention is to suppress the production of Desaccharified Compound (2) in the L-cysteine-containing formulation, and to accomplish further stabilization of the formulation.

Solution to Problem

As a result of extensive study, when preparing the lyophilized amrubicin formulation, the present inventors have found that the production of Desaccharified Compound (2) can be suppressed by controlling the concentration of amrubicin or a pharmaceutically acceptable salt thereof in the aqueous solution before lyophilization within a certain definite range and using L-cysteine or a salt thereof together, by which a lyophilized formulation being stable even in a long term storage can be obtained. Namely, the present inventions are as follows.

[1] A process of a lyophilized amrubicin formulation comprising the following Steps (1) to (3):

(1) preparing an aqueous solution comprising (a) amrubicin or a pharmaceutically acceptable salt thereof and (b) L-cysteine or a salt thereof wherein the concentration of amrubicin or a pharmaceutically acceptable salt thereof is in the range of about 7.5 mg(potency)/mL to about 30 mg(potency)/mL, (2) sterilizing the aqueous solution of Step (1) by filtration, and (3) lyophilizing the aqueous solution obtained in Step (2).

[2] The process of [1] wherein the salt of L-cysteine is a hydrochloride thereof.

[3] The process of [1] or [2] wherein the salt of amrubicin is a hydrochloride thereof.

[4] The process of any one of [1] to [3] wherein the concentration of amrubicin or a pharmaceutically acceptable salt thereof in the aqueous solution in Step (1) is in the range of about 7.5 mg(potency)/mL to about 25 mg(potency)/mL.

[5] The process of any one of [1] to [4] wherein the aqueous solution of Step (1) further comprises an excipient.

[6] The process of [5] wherein the excipient is lactose.

[7] The process of any one of [1] to [6] wherein the salt of amrubicin is a crystalline amrubicin hydrochloride showing main peaks in a powder X-ray diffraction pattern at the diffraction angles ($2\theta$) of 6.3±0.3, 10.1±0.3, 20.3±0.3, 26.5±0.3 and 26.9±0.3.

[8] A lyophilized formulation comprising amrubicin or a pharmaceutically acceptable salt thereof which is prepared by lyophilizing an aqueous solution comprising amrubicin or a pharmaceutically acceptable salt thereof in the range of about 7.5 mg(potency)/mL to about 30 mg(potency)/mL.

[9] The lyophilized formulation of [8] comprising L-cysteine or a salt thereof.

[10] The lyophilized formulation of [9] wherein the L-cysteine or a salt thereof is contained in the range of about 0.5 mg to about 250 mg per 100 mg (potency) of amrubicin or a salt thereof.

[11] The lyophilized formulation of [9] wherein the L-cysteine or a salt thereof is contained in the range of about 3 mg to about 45 mg per 100 mg (potency) of amrubicin or a salt thereof.

[12] The lyophilized formulation of any one of [8] to [11] wherein the salt of amrubicin is a hydrochloride thereof.

[13] The lyophilized formulation of any one of [9] to [12] wherein the salt of L-cysteine is a hydrochloride thereof.

[14] The lyophilized formulation of any one of [8] to [13] wherein the water content of the formulation is in the range of 0 wt % to about 4 wt % based on the weight of the lyophilized powder.

[15] The lyophilized formulation of any one of [8] to [13] wherein the water content of the formulation is in the range of about 0.5 wt % to about 3.5 wt % based on the weight of the lyophilized powder.

[16] The lyophilized formulation of any one of [8] to [13] wherein the water content of the formulation is in the range of about 0.5 wt % to about 2.0 wt % based on the weight of the lyophilized powder.

[17] The lyophilized formulation prepared by the process of any one of [1] to [7].

Effects of Invention

The present invention can suppress the production of the desaccharified compound (i.e. a degradation product of amrubicin), which are achieved by controlling the concentration of amrubicin or a pharmaceutically acceptable salt thereof in the aqueous solution before lyophilization within a certain definite range and using L-cysteine or a salt thereof together, by which a lyophilized formulation being stable even in a long term storage can be obtained.

BEST MODE FOR CARRYING OUT INVENTION

Figure 1:
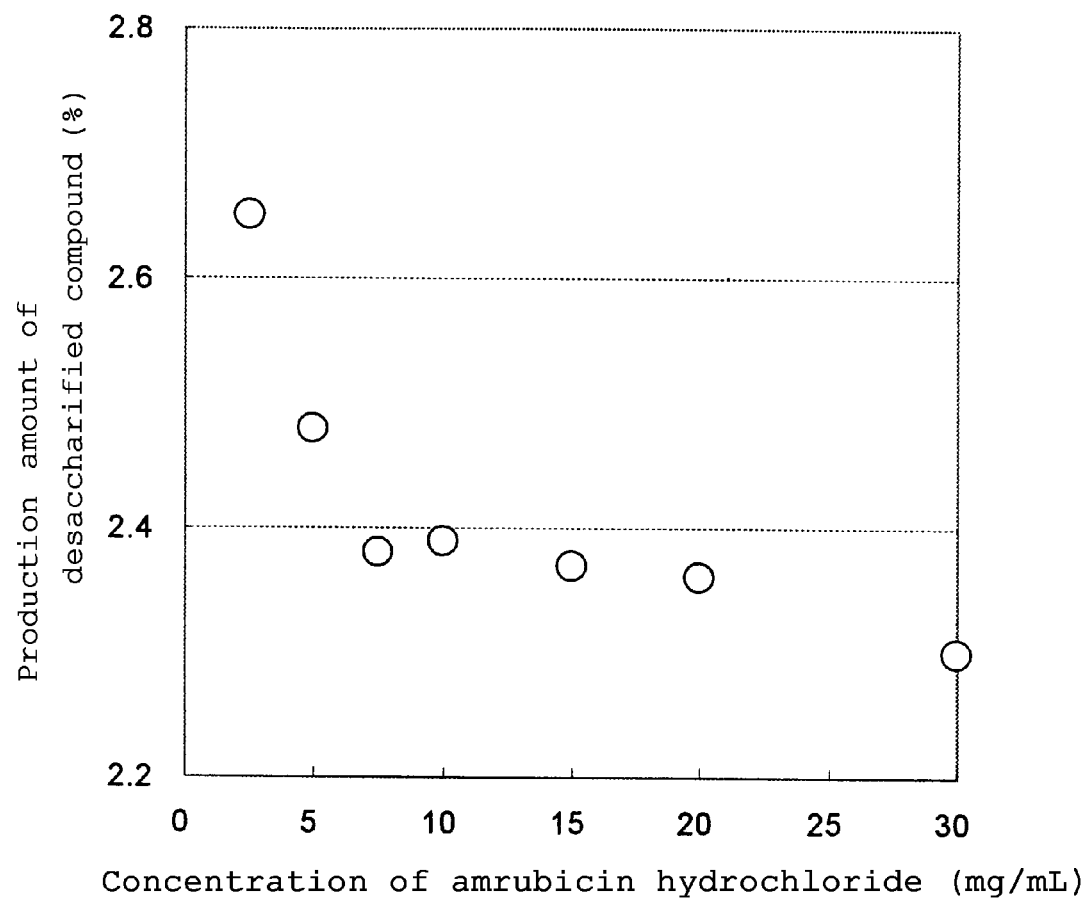
FIG. 1 is a graph showing the production amount of Desaccharified Compound (2), which is one of the degradation products, in the lyophilized formulations after a stability test at 40° C. for 3 months (Example 1). The tested formulations were manufactured by lyophilizing several aqueous solutions having various concentrations of amrubicin hydrochloride in a compact freezing-drying machine.

Hereinafter, the present invention is explained in more detail.

In the present description, unless otherwise noted, the amounts of Desaccharified Compound (2) and Deaminated Compound (3) are expressed in percentage by weight based on the weight of the amrubicin. The amounts of Desaccharified Compound (2) and Deaminated Compound (3) can be measured by HPLC method using absolute calibration curve method based on reference standards of amrubicin.

In the present description, unless otherwise noted, the "water content" of the formulation is expressed in percentage by weight based on the weight of the lyophilized powder. The water content of the formulation can be measured by well-known methods such as Karl Fischer's method.

The pharmaceutically acceptable salt of amrubicin used herein includes acid addition salts and base addition salts. The acid addition salts used herein include, for example, inorganic acid salts such as hydrochloride, hydrobromide, sulfate, hydroiodide, nitrate, and phosphate; and organic acid salts such as citrate, oxalate, acetate, formate, propionate, benzoate, trifluoroacetate, fumarate, maleate, tartrate, aspartate, glutamate, methanesulfonate, benzenesulfonate, and camphorsulfonate. The base addition salts used herein include, for example, inorganic base salts such as sodium salt, potassium salt, calcium salt, magnesium salt, and ammonium salt; and organic base salts such as triethylammonium salt, triethanolammonium salt, pyridinium salt, and diisopropylammonium salt. Preferably, the pharmaceutically acceptable salt of amrubicin used herein is, for example, hydrochloride.

When amrubicin is in the form of amrubicin hydrochloride, it is preferable to use β type crystalline amrubicin hydrochloride [i.e. a crystal whose main peaks in a powder X-ray diffraction pattern are diffraction angles ($2\theta$) of 6.3±0.3, 10.1±0.3, 20.3±0.3, 26.5±0.3 and 26.9±0.3 (JP 2975018 B)] which is more stable than other types of crystalline amrubicin hydrochloride. The powder X-ray diffraction pattern can be measured by an X-ray diffractometer (RINT 2500 V, manufactured by RIGAKU DENKI CORPORATION) with Cu.Kα radiation ($\lambda$=1.541 Å).

L-cysteine or a salt thereof may be added as an amino acid to stabilize the lyophilized formulation of the present invention. The salt of L-cysteine used herein is generally L-cysteine hydrochloride, and other salts thereof include, for example, L-cysteine sulfate. The L-cysteine or a salt thereof used herein may also be in the form of a solvate such as a hydrate. A preferred example thereof includes L-cysteine hydrochloride monohydrate.

The addition of L-cysteine or a salt thereof to the lyophilized formulation of the present invention is not limited to a particular amount or procedure. Considering factors such as the stability of amrubicin and the pharmacological action of other additives, the adequate amount of L-cysteine or a salt thereof is, for example, in the range of about 0.5 mg to about 250 mg, preferably in the range of about 3 mg to about 80 mg, and more preferably in the range of about 3 mg to about 45 mg per 100 mg (potency) of amrubicin or a pharmaceutically acceptable salt thereof. It is particularly preferable to add L-cysteine in an amount of about 5 mg to about 20 mg, or a salt of L-cysteine in the corresponding amount thereto, per 100 mg (potency) of amrubicin or a salt thereof. The "salt of L-cysteine in the corresponding amount thereto" used herein means that the L-cysteine contained in the salt is equimolar amount to the former free L-cysteine. For example, the amount of L-cysteine hydrochloride and L-cysteine hydrochloride monohydrate corresponding to 121.2 mg of L-cysteine are 157.6 mg and 175.6 mg respectively. In case that L-cysteine hydrochloride monohydrate is used as a salt of L-cysteine, the amount corresponding to "the range of about 5 mg to about 20 mg of L-cysteine" is the range of about 7.2 mg to about 29 mg of L-cysteine hydrochloride monohydrate.

If necessary, additives (e.g. an excipient which may be added to a formulation as a typical ingredient) may be added to the lyophilized formulation of the present invention. The excipient used herein includes, for example, lactose, sucrose, palatinose, glucose, maltose, fructose, mannitol, erythritol, xylitol, maltitol, inositol, dextran, sorbitol, albumin, and a mixture containing two or more thereof. A preferred excipient used herein includes, for example, lactose, sucrose, glucose, maltose, fructose, mannitol, xylitol, inositol, dextran, and a mixture containing two or more thereof. More preferably, the excipient includes lactose, mannitol and a mixture thereof. The amount of excipient used herein is not limited to a particular amount as long as the present invention exhibits its effects, and may optionally vary based on factors such as feeling of use and anticancer effects.

In order to stabilize the lyophilized formulation of the present invention, it is effective to keep the water content of the lyophilized formulation in the range of 0 wt % to about 4 wt %, preferably in the range of 0 wt % to about 3.5 wt %, more preferably in the range of about 0.5 wt % to about 3.5 wt %, and even more preferably in the range of about 0.5 wt % to about 2.0 wt %.

The lyophilized formulation is prepared by, for example, dissolving (a) amrubicin or a pharmaceutically acceptable salt thereof, (b) L-cysteine or a salt thereof, and an optional excipient and the like in distilled water for injection, sterilizing the mixed solution by filtration, loading a vial bottle with the filtrated solution, and then subjecting the vial bottle to lyophilization to give a product thereof in a powder state. Injections are stored in this state, and are dissolved in water before use for administration.

The feature of the present invention is to control the concentration of amrubicin or a pharmaceutically acceptable salt thereof in the aqueous solution before lyophilization in the above-mentioned process at about 7.5 mg(potency)/mL or more. As shown in the following Examples, the present inventors have found that the lyophilized formulations in which the concentration of amrubicin in the aqueous solution before lyophilization is about 7.5 mg(potency)/mL or more show a higher stability than the lyophilized formulations in which the concentration of that is less than 7.5 mg(potency)/mL. The concentration of amrubicin or a pharmaceutically acceptable salt thereof in the aqueous solution before lyophilization is preferably about 8.0 mg(potency)/mL or more, and more preferably about 9.0 mg(potency)/mL or more.

The upper limit of the concentration of amrubicin or a pharmaceutically acceptable salt thereof in the aqueous solution before lyophilization is not limited to a particular amount as long as the components thereof are dissolved. Preferably, the concentration is about 90 mg(potency)/mL or less. Considering factors in the manufacturing process (e.g. solubility and control of the fluid volume), the concentration of amrubicin or a pharmaceutically acceptable salt thereof is more preferably about mg(potency)/mL or less, even more preferably about 25 mg(potency)/mL or less, and particularly more preferably about 20 mg(potency)/mL or less.

Furthermore, it is preferable to control the pH value of the aqueous solution, wherein (a) amrubicin or a pharmaceutically acceptable salt thereof, (b) L-cysteine or a salt thereof, and an optional excipient and the like are dissolved in distilled water for injection, by adding a small amount of a base and/or acid before sterilizing it by filtration. Considering the property of amrubicin, it is preferable to adjust the pH value to the range of about 1.9 to about 5.0, and it is more preferable to adjust the pH value to the range of about 1.9 to about 3.0. A base which can be used as a pH adjuster herein includes, for example, an alkali metal hydroxide such as sodium hydroxide and potassium hydroxide, an alkaline earth metal hydroxide such as magnesium hydroxide and calcium hydroxide, and a mild-acidic alkali metal salt. A preferred base which can be used as a pH adjuster herein includes, for example, sodium hydroxide and potassium hydroxide. An acid which can be used as a pH adjuster herein includes, for example, hydrochloric acid and sulfuric acid.

The stabilized lyophilized-formulation of the present invention comprising amrubicin or a pharmaceutically acceptable salt thereof can be used as a cancer chemotherapeutic agent for treating various cancerous diseases. The cancerous diseases include, for example, hematological cancers and solid cancers, and should not be limited to a particular disease. When treating human beings by intravenous administration, for example, the daily dosage thereof is preferably in the range of 5 mg to 300 mg, more preferably in the range of 20 mg to 250 mg, and even more preferably in the range of 35 mg to 160 mg per body surface area of the human being ($m^2$), which may be given by continuous infusion. The administration schedule thereof includes, for example, a single administration and a once-daily administration for 3 days.

EXAMPLE

Hereinafter, the present inventions are illustrated more specifically by Examples, but the present inventions should not be construed to be limited thereto. In the following Examples and Tests, β-type crystalline amrubicin hydrochloride was used, which was prepared by the process disclosed in JP 2975018B.

Example 1

Storage Stability of the Lyophilized Formulation Prepared by a Compact Freezing-drying Machine 20 Mg (potency) of amrubicin hydrochloride was added with 3.2 mg of L-cysteine hydrochloride monohydrate, 50 mg of lactose as an excipient, and 0.13 mg of sodium hydroxide as a pH adjuster to 8 mL, 4 mL, 2.67 mL, 2 mL, 1.33 mL, 1 mL, and 0.67 mL of distilled water for injection in order to prepare solutions wherein each concentration of amrubicin hydrochloride is 2.5 mg/mL, 5 mg/mL, 7.5 mg/mL, 10 mg/mL, 15 mg/mL, 20 mg/mL, and 30 mg/mL, respectively. Then, each solution was sterilized by filtration and put into a glass vial. Each vial was put into a compact freezing-drying machine (capacity of drying chamber is about 0.5 m$^3$) (manufactured by ULVAC, DFM-13A-TOKU) and completely frozen. Then, water was dried while controlling the temperature and the degree of vacuum so that the lyophilized cake would not melt. Then, each vial was sealed with a rubber stopper and cap seal to obtain lyophilized formulations. The water content of each lyophilized formulation was measured to confirm that all of the lyophilized formulations were completely dried. Then, a storage stability test was carried out with the lyophilized formulations at 40° C. for a month and 3 months. Table 1 shows the measurement results of Desaccharified Compound (2) and Deaminated Compound (3) which are the degradation products (measured by HPLC method). FIG. 1 shows a graph of the measurement result of Desaccharified Compound (2) tested at 40° C. for 3 months.

TABLE 1

| Amrubicin hydrochloride concentration (mg/mL) | Initial water content (%) | Desaccharified Compound (%) | | | Deaminated Compound (%) | | |
|---|---|---|---|---|---|---|---|
| | | Initial | 40° C. for 1 month | 40° C. for 3 months | Initial | 40° C. for 1 month | 40° C. for 3 months |
| 2.5 (Comparative Example) | 0.9 | 0.21 | 1.54 | 2.65 | 0.03 | 0.10 | 0.16 |
| 5.0 (Comparative Example) | 0.8 | 0.20 | 1.31 | 2.48 | 0.03 | 0.10 | 0.16 |
| 7.5 | 0.8 | 0.20 | 1.28 | 2.38 | 0.03 | 0.10 | 0.16 |
| 10 | 0.8 | 0.20 | 1.23 | 2.39 | 0.03 | 0.09 | 0.16 |
| 15 | 0.8 | 0.19 | 1.24 | 2.37 | 0.03 | 0.10 | 0.16 |
| 20 | 0.8 | 0.20 | 1.20 | 2.36 | 0.03 | 0.10 | 0.16 |
| 30 | 0.9 | 0.20 | 1.21 | 2.30 | 0.03 | 0.10 | 0.16 |

As shown in the above stability data, it has been found that the production amount of Desaccharified Compound (2) after the storage of lyophilized formulation for a long period depends on the concentration of amrubicin hydrochloride in the aqueous solution before lyophilization. Namely, it has been found that the lyophilized formulations prepared by making the concentration of amrubicin hydrochloride in the range of 7.5 mg/mL to 30 mg/mL can be improved on stability, in particular, the production of Desaccharified Compound (2) can be suppressed compared with Comparative Examples (i.e. lyophilized formulations prepared by making the concentration of amrubicin hydrochloride at 2.5 mg/mL and 5.0 mg/mL). Thus, such lyophilized formulations are perceived to be sufficiently stable for long-period storage. In addition, the production amount of Deaminated Compound (3) did not depend on the concentrations of amrubicin hydrochloride, and it was low in all of the concentrations.

Example 2

Figure 2:
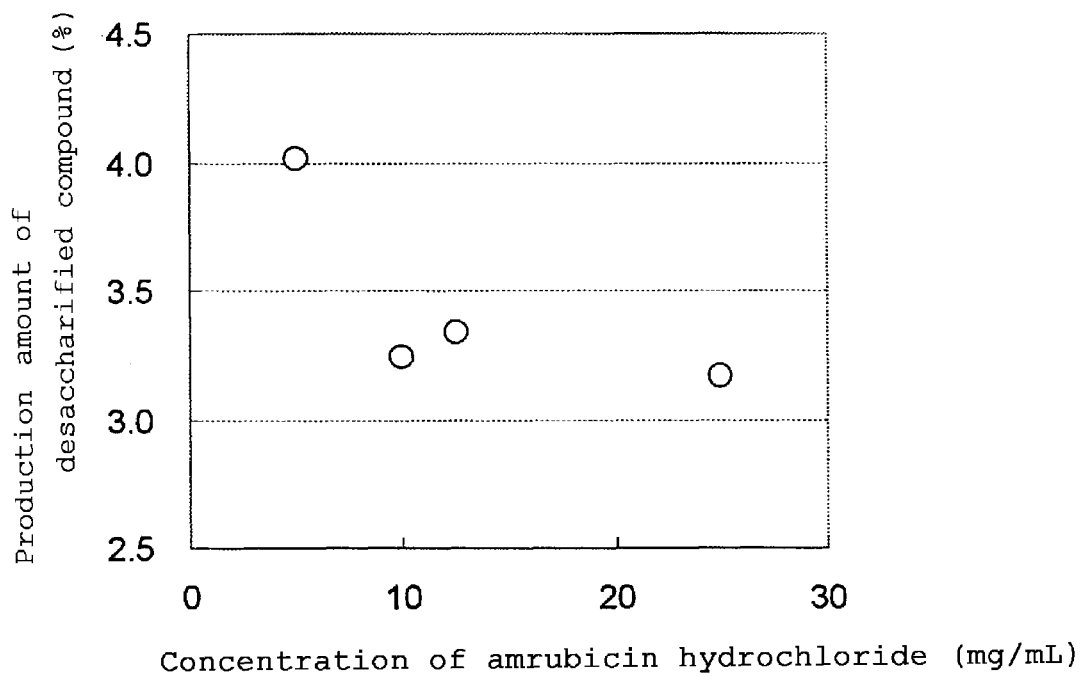
FIG. 2 is a graph showing the production amount of Desaccharified Compound (2), which is one of the degradation products, in the lyophilized formulations after a stability test at 40° C. for 6 months (Example 2). The tested formulations were manufactured by lyophilizing several aqueous solutions having various concentrations of amrubicin hydrochloride in a large freezing-drying machine.

Storage Stability of the Lyophilized Formulation Prepared by a Large Freezing-drying Machine 50 Mg (potency) of amrubicin hydrochloride was added with 8 mg of L-cysteine hydrochloride monohydrate, 125 mg of lactose as an excipient, and 0.31 mg of sodium hydroxide as a pH adjuster to 10 mL, 5 mL, 4 mL, and 2 mL of distilled water for injection in order to prepare solutions wherein each concentration of amrubicin hydrochloride is 5 mg/mL, 10 mg/mL, 12.5 mg/mL, and 25 mg/mL, respectively. Then, each solution was sterilized by filtration and put into a glass vial. Each vial was put into a large freezing-drying machine (capacity of drying chamber is about 12.4 m$^3$) (manufactured by ULVAC, DFB5150-5BS-ST/CIP/CCV) and completely frozen. Then, water was dried while controlling the temperature and the degree of vacuum so that the lyophilized cake would not melt. Then, each vial was sealed with a rubber stopper and cap seal to obtain lyophilized formulations. The water content of each lyophilized formulation was measured to confirm that all of the lyophilized formulations were completely dried. Then, a storage stability test was carried out with the lyophilized formulations at 40° C. for a month, 3 months and 6 months. Table 2 shows the measurement results of Desaccharified Compound (2) which is the degradation product (measured by HPLC method). FIG. 2 shows a graph of the measurement result of Desaccharified Compound (2) tested at 40° C. for 6 months.

TABLE 2

| Amrubicin hydrochloride concentration (mg/mL) | Initial water content (%) | Desaccharified Compound (%) | | | |
|---|---|---|---|---|---|
| | | Initial | 40° C. for 1 month | 40° C. for 3 month | 40° C. for 6 months |
| 5.0 (Comparative Example) | 0.8 | 0.24 | 2.13 | 2.93 | 4.01 |
| 10 | 1.0 | 0.20 | 1.26 | 2.21 | 3.24 |
| 12.5 | 0.7 | 0.23 | 1.32 | 2.27 | 3.34 |
| 25 | 0.8 | 0.47 | 1.40 | 2.21 | 3.17 |

As shown in the above stability data, it has been found that the production amount of Desaccharified Compound (2) after the storage of lyophilized formulation for a long period depends on the concentration of amrubicin hydrochloride in the aqueous solution before lyophilization. Namely, it has been found that the lyophilized formulations prepared by making the concentration of amrubicin hydrochloride in the range of 10 mg/mL, 12.5 mg/mL, and 25 mg/mL can suppress the production of Desaccharified Compound (2) compared with Comparative Examples (i.e. lyophilized formulations prepared by controlling the concentration of amrubicin hydrochloride at 5 mg/mL). Thus, such lyophilized formulations are perceived to be sufficiently stable for long-period storage.

As described above, the present invention provides a further stabilized form of the lyophilized amrubicin formulation, and thereby the formulation is expected to be stable to store for a prolonged period.

Industrial Applicability

The present invention has a wide variety of industrial applications because it provides a lyophilized formulation which is sufficiently stable to store for a long period and comprises amrubicin useful as a cancer chemotherapeutic agent.

The invention claimed is:
1. A process for preparing a lyophilized amrubicin formulation comprising the following Steps (1) to (3):
 (1) preparing an aqueous solution comprising (a) amrubicin or a pharmaceutically acceptable salt thereof and (b) L-cysteine or a salt thereof wherein the concentration of amrubicin or a pharmaceutically acceptable salt thereof is in the range of 7.5 mg(potency)/mL to 30 mg(potency)/HmL, (2) sterilizing the aqueous solution of Step (1) by filtration, and (3) lyophilizing the aqueous solution obtained in Step (2).

2. The process of claim 1 wherein the salt of L-cysteine is a hydrochloride thereof.

3. The process of claim 1 or 2 wherein the salt of amrubicin is a hydrochloride thereof.

4. The process of claim 1 wherein the concentration of amrubicin or a pharmaceutically acceptable salt thereof in the aqueous solution in Step (1) is in the range of 7.5 mg(potency)/mL to 25 mg(potency)/mL.

5. The process of claim 1, wherein the aqueous solution of Step (1) further comprises an excipient.

6. The process of claim 5 wherein the excipient is lactose.

7. The process of claim 1, wherein the salt of amrubicin is a crystalline amrubicin hydrochloride showing main peaks in a powder X-ray diffraction pattern at the diffraction angles ($2\theta$) of $6.3 \pm 0.3$, $10.1 \pm 0.3$, $20.3 \pm 0.3$, $26.5 \pm .3$ and $26.9 \pm 0.3$.

8. A lyophilized formulation comprising amrubicin or a pharmaceutically acceptable salt thereof which is prepared by lyophilizing an aqueous solution comprising amrubicin or a pharmaceutically acceptable salt thereof in the range of 7.5 mg potency)/mL to 30 mg(potency)/mL, and wherein the lyophilized formulation further comprises L-cysteine or a salt thereof.

9. The lyophilized formulation of claim 8, wherein the L-cysteine or a salt thereof is contained in the range of 0.5 mg to 250 mg per 100 mg (potency) of amrubicin or a salt thereof.

\* \* \* \* \*